United States Patent [19]

Merilan et al.

[11] 4,390,633

[45] Jun. 28, 1983

[54] DETERMINING REPRODUCTIVE STATUS OF MAMMALS WITH NMR OF CERVICAL MUCUS

[75] Inventors: Charles P. Merilan; Jerald R. Sears, both of Columbia, Mo.

[73] Assignee: The Curators of the University of Missouri, Columbia, Mo.

[21] Appl. No.: 286,593

[22] Filed: Jul. 24, 1981

[51] Int. Cl.$^3$ .................... G01N 33/48; G01N 24/08
[52] U.S. Cl. .................................. 436/65; 436/173; 436/906
[58] Field of Search ................ 23/230 B, 917; 436/65, 436/173, 906

[56] References Cited

U.S. PATENT DOCUMENTS 3,436,186 4/1969 McSweeney .................... 23/917
3,955,928 5/1976 Yee ................................ 436/65
3,986,494 10/1976 Preti .............................. 436/65 X

OTHER PUBLICATIONS

D. F. Katz et al., Biology of Reproduction, 17, 843-849 (1978).

Primary Examiner—Sidney Marantz
Attorney, Agent, or Firm—Senniger, Powers, Leavitt and Roedel

[57] ABSTRACT

A method for determining the reproductive status of mammals involves the steps of obtaining at periodic time intervals mucus samples from the cervix of a mammal, obtaining nuclear magnetic resonance spectra of the samples using a narrow line nuclear magnetic resonance spectrometer, determining the nuclear magnetic resonance ratios from the spectra on the basis of the relationship $$\frac{\text{peak width at half amplitude}}{\text{peak height}}$$

and thereafter evaluating the reproductive status of the mammal from such ratios.

8 Claims, 5 Drawing Figures

DETERMINING REPRODUCTIVE STATUS OF MAMMALS WITH NMR OF CERVICAL MUCUS

BACKGROUND OF THE INVENTION

This invention relates to methods for determining pregnancy or reproductive status in mammals such as cattle and, more particularly, to such methods which are novel and which provide a relatively simple and clear-cut interpretation of the reproductive status of mammals.

In the past, there have been various test methods for determining the status of mammalian females in their reproductive cycle, i.e. fertile period, non-fertile period, pregnancy, and abnormal conditions.

In general, such prior methods have been species dependent, but typically involve cyclic physiological or behavioral events such as menstrual periods in humans and primates and estrus behavior in domestic animals. Manual palpation of the reproductive tract and associated structures has been the accepted diagnostic method with large domestic animals and laproscopic techniques have been applied to many species. More recently, hormone assays of body fluids have been used experimentally with several species. These assays, while believed to be accurate, are generally quite time-consuming.

The observational methods of the prior art as applied to domestic animals are reported to be only 60% effective. Further, manual palpation is skill-limited and, moreover, is typically used for pregnancy diagnosis only after approximately 40 days past breeding. Laproscopy has the disadvantage of involving surgical procedures. Finally, hormone assays generally are still experimental procedures and as with progesterone, they may be effective only during brief specific time periods.

Illustrative prior art patents in this field include U.S. Pat. No. 3,826,616, U.S. Pat. No. 3,926,037, U.S. Pat. No. 3,955,928, U.S. Pat. No. 3,982,423, U.S. Pat. No. 3,979,945 and U.S. Pat. No. 4,016,250.

Attention is also directed to a publication by Katz et al. Biology of Reproduction 17, 843–849 (1978) entitled "Water Mobility Within Bovine Cervical Mucus" which deals with the self-diffusion coefficient of water with sperm-free bovine cervical mucus measured by pulsed-gradient nuclear magnetic resonance (NMR) spectroscopy; and Odeblad et al. Chapter 14 entitled "Types of Cervical Secretions: Biophysical Characteristics" from "The Biology of the Cervix", The University of Chicago Press (1973).

There remains, therefore, an unfulfilled need for a simple and clean-cut procedure of acceptable reliability for determining the reproductive status of female mammals.

SUMMARY OF THE INVENTION

Among the several objects of the invention may be noted the provision of a method for determining pregnancy of reproductive status in mammals which is relatively simple and convenient to practice; the provision of such a method which involves a detailed biophysical assay of mucus from the female mammal; the provision of a method of the type described wherein the assay value obtained in indicative of the reproductive status of the individual mammal and pregnancy can be determined within 16–20 days post-breeding in dairy cattle, for example, and the provision of such a method which has application to humans and primates as well as both domestic and non-domestic animals from which cervical mucus samples can be obtained. Other objects and features will be in part apparent and in part pointed out hereinafter.

Briefly, then, the present invention is directed to the method for determining pregnancy or reproductive status in mammals which comprises the steps of (a) obtaining at periodic time intervals mucus samples from the cervix of a mammal whose reproductive status is to be determined; (b) obtaining nuclear magnetic resonance spactra of such samples; (c) determining the nuclear magnetic resonance ratios from such spectra on the basis of the relationship $$\frac{\text{peak width at half amplitude}}{\text{peak height}} \text{ or } \frac{\text{peak height}}{\text{peak width at half amplitude}}$$

and (d) evaluating the reproductive status of said mammal from said ratios. The present invention also includes other features as will be described hereinafter.

DESCRIPTION OF THE PREFERRED EMBODIMENTS

In accordance with the present invention, it has now been found that an improved method for determining pregnancy or reproductive status in a mammal involves the steps of obtaining at periodic time intervals mucus samples from the cervix of a mammal whose reproductive status is to be determined, obtaining nuclear magnetic resonance spactra of the mucus samples, determining the nuclear magnetic resonance ratios from the spectra on the basis of the relationship.

$$\frac{\text{peak width at half amplitude}}{\text{peak height}}$$

and evaluating the reproductive status of the mammal from said ratios. Underlying the present invention is our finding that mucus spectral line shapes, as measured by the ratio $$\frac{\text{peak width at half amplitude}}{\text{peak height}}$$

are related to the reproductive status of mammals. Such ratio values begin to decline prior to the onset of estrus, decline rapidly during estrus reaching a low point in late standing heat, and thereafter rise gradually to the values associated with the diestrus condition or the higher values characteristic of pregnancy.

In carrying out the method of the present invention, a mucus sample is first obtained, with the aid of a speculum and penlight, from the cervical os of the mammal involved. Care is taken to avoid penetrating the cervix in order to minimize any adverse effects upon the cervical plug of a pregnant mammal. Approximately 0.1 ml. of the mucus sample thus obtained is then transferred into a capillary nuclear magnetic resonance (NMR) tube at a temperature of approximately 4° C. to 40° C., preferably 20° C. Larger mucus samples, e.g. 0.75 ml. mucus sample in a standard 5 mm diameter NMR tube may be used but are not necessary and may be difficult to obtain.

The NMR spectrum of the sample is next obtained by placing the sample tube in the detection probe of a Narrow Line NMR spectrometer. For this purpose, a Varian T-60 or a Varian EM-360 spectrometer operated at a frequency of 60 MHz produces satisfactory results. Higher frequencies may be utilized, but in general we prefer to operate at frequencies between 60 MHz and 200 MHz. The major constituent in mucus is water and the variations in both the amount and characteristics of water are determined by observing its protons.

The determination of the nuclear magnetic resonance ratio on the basis of the relationship $$\frac{\text{peak width at half amplitude}}{\text{peak height}} \text{ or } \frac{\text{peak height}}{\text{peak width at half amplitude}}$$

provides a first order approximation of peak shape and, in accordance with the present invention, enables one to evaluate the reproductive status of the mammal involved. Increased peak width for the proton spectrum of the cervical mucus is an indication of a multiplicity of water binding sites in the mucus.

Figure 1:
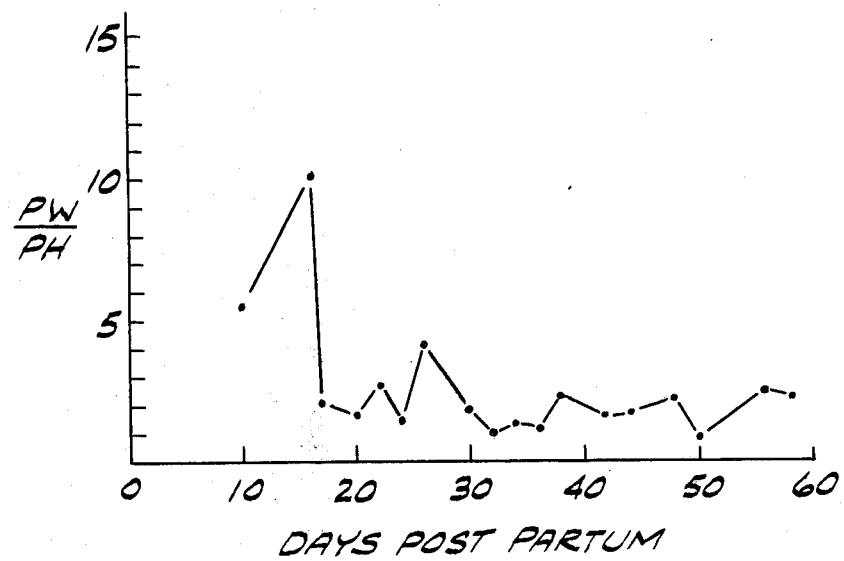
FIG. 1 is a graph showing the method of the present invention carried out to obtain data on a cow reflecting PW/PH ratios versus days post partum.

Referring to FIG. 1 of the drawings, the method of the present invention was carried out to obtain the aforementioned ratio PW/PH for a series of sequential mucus sample spectra from a cow from 10 to 58 days post partum (post birth). The general pattern shown is typical of the post partum spectra for such animals in that the peak ratios are quite variable but generally high for a period following calving. The ratios then decline and exhibit a periodic low level fluctuation.

Figure 2:
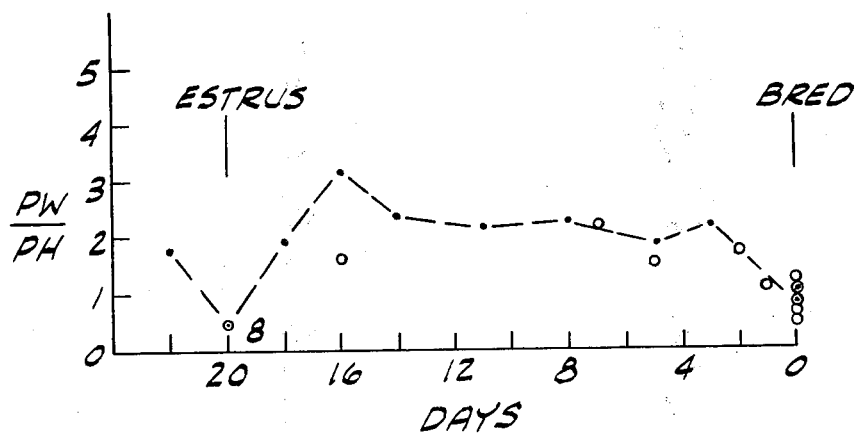
FIG. 2 is a graph showing the method of the present invention carried out to obtain data on cows reflecting the PW/PH ratios versus days during the estrous cycle of the cows.

Referring to FIG. 2 of the drawings, the pattern of NMR PW/PH ratios determined in accordance with the present invention during the estrous cycle of cows is shown in two ways. The dashed line represents the mean values for 4 animals sampled every third day and standardized to a composite 20 day cycle. The open circles represent the results from individual samples from 14 other animals which were obtained in routine herd group samplings and without any adjustment for their individual cycle lengths. FIG. 2 thus shows good agreement in the pattern of variation in peak ratios during the estrous cycle.

Figure 3:
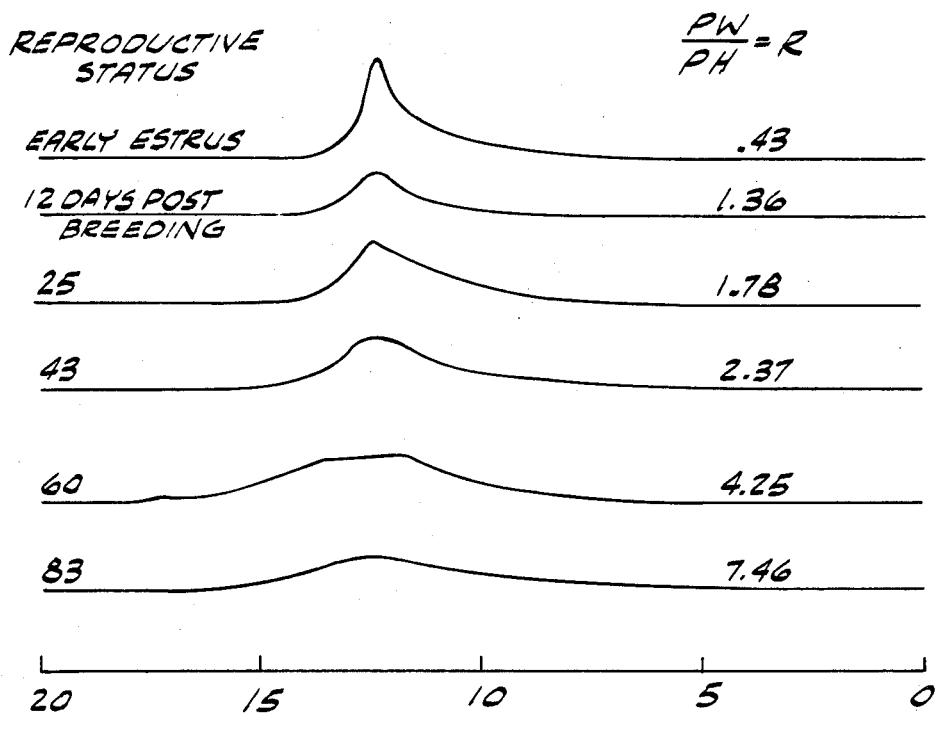
FIG. 3 is a graph of the tracings of actual NMR spectra from the mucus samples of individual bovine animals sampled at different times subsequent to being bred at their last observed heat periods.

Referring to FIG. 3 of the drawings, there is shown the tracings of actual NMR spectra from the mucus samples of individual bovine animals sampled at different reproductive stages with the PW/PH ratios being set forth, in accordance with the practice of the method of the present invention. The early estrus sample spectrum closely resembles that of distilled water, whereas, as indicated, the amplitude decreases and peak width increases during gastation. This demonstrates graphically the manner in which the method of the present invention enables one to evaluate the reproductive status of the animals involved at various stages of the estrus and post-estrus cycle. It should be noted that in early heat the NMR spectrum shows a sharp peak but that the peak keeps spreading further and further as the cycle progresses with the PW/PH ratios rising accordingly.

Figure 4:
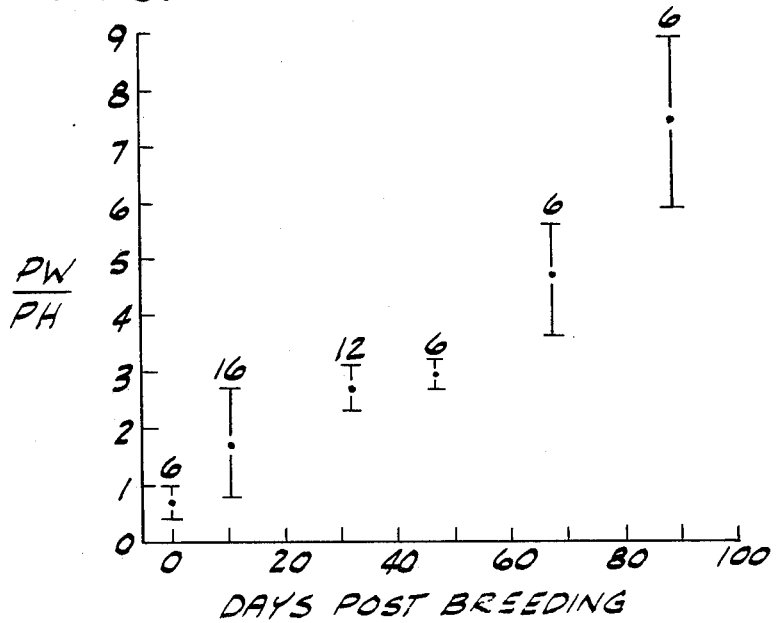
FIG. 4 is a graph of the results obtained through the practice of the present invention with 54 Holstein cows and showing the respective PW/PH ratios versus days past breeding.

Referring to FIG. 4 of the drawings and again in accordance with the practice of the method of the present invention, there is shown the results for 54 Holstein cows summarized from herd group samplings in which all instrumental parameters were constant and the cows were not involved in other research projects incorporating either severe stress factors or endocrine level manipulation. The post-breeding data have been blocked into 20 day units and averaged (both days and PW/PH ratios), and for each grouping the figure given shows the number of animals, the mean is represented by a dot and ± standard deviation is indicated by the connected bars located equidistant above and below each mean. More particularly, the first data grouping includes all stages of the estrous cycle with the expected larger variance than is found in either the 12-40 or 41-60 day groups. The increased variation found in the 61-80 and 81-99 day groups appears to be an accurate reflection of the highly individualized ratio patterns of cows in mid-gestation. Additional data to 205 days post partum indicates that the pattern appears to be one of reaching and holding at a maxima following 3-4 months postbreeding. This maximum ratio varies for different mammals.

Figure 5:
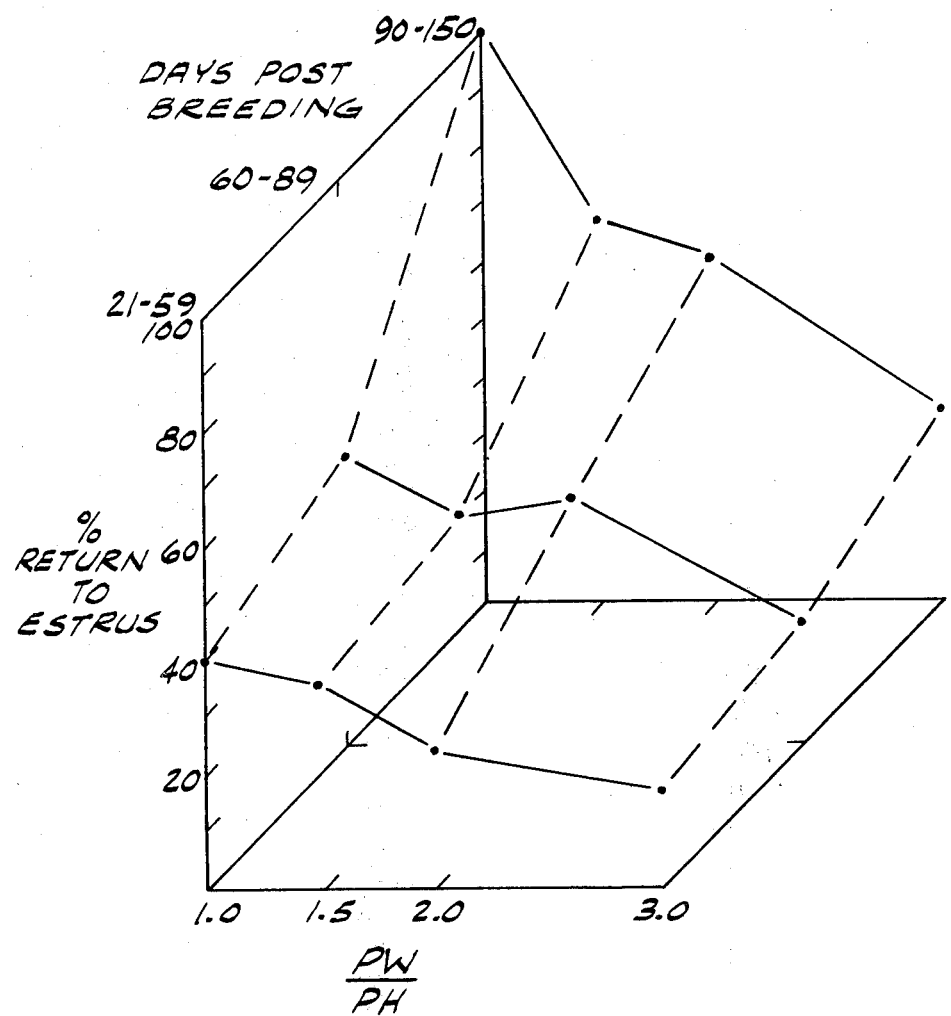
FIG. 5 is a graph showing the relationship between the PW/PH ratios, % return to estrus and days post breeding.

Referring to FIG. 5 of the drawings, there is presented as a response surface the percent of animals which returned to heat after pregnancy was confirmed. As shown, the effects of the PW/PH ratio and stage of gestation, when considered jointly, clearly indicate that as gestation proceeds, low ratio PW/PH values are highly indicative of impending pregnancy termination, thus indicating that the method of the present invention has potential prognostic value.

In Tables I and II are presented the data obtained when the method of the present invention was carried out with groups of cows in different categories with the individual ratios being given for each of one or more tests on the animals for each test period indicated. The manner in which the PW/PH ratios cycle, or vary, during the test periods set forth can readily be discerned. Thus, the PW/PH ratio values begin to decline prior to the onset of estrus, decline rapidly during estrus and reach a low point in late standing heat. In heat, the ratio values will generally be below 0.8 and all the way down to 0.25. As shown, the ratio values then begin to increase during the postbreeding period. Also, as indicated from the data set forth in Table I, the method of the present invention achieves an accuracy of approximately 70% in determining the reproductive status of the animals involved in the test. Further, the method of this invention permits results to be obtained earlier than and without the rigorous time interval restrictions associated with radioimmunoassay methods and, moreover, is advantageously less time-consuming.

TABLE I

| Days Postbreeding | PW/PH Ratio | Total Animals | Calved | + Test Correct | Did Not Calve | − Test Correct | + And − Test Correct | Errors False + | False − |
|---|---|---|---|---|---|---|---|---|---|
| +2 to +22 | | 20 | 7 | | 13 | | | | |
| | <1 | | | 1 | | 10 | 11 | 3 | 6 |
| | 1-2 | | | 4 | | 10 | 14* | 3 | 3 |
| | >1 | | | 6 | | 3 | 9 | 10 | 1 |
| | >2 | | | 2 | | 6 | 8 | 7 | 5 |
| +23 to +59 | | 31 | 11 | | 20 | | | | |
| | <1 | | | 1 | | 16 | 17 | 4 | 10 |
| | 1-1.5 | | | 6 | | 14 | 20* | 6 | 5 |
| | 1-2 | | | 7 | | 10 | 17 | 10 | 4 |
| | 1-2.5 | | | 8 | | 9 | 17 | 11 | 3 |
| | >1 | | | 10 | | 4 | 14 | 16 | 1 |
| | >2 | | | 3 | | 14 | 17 | 6 | 8 |
| | >2.5 | | | 2 | | 15 | 17 | 5 | 9 |
| +60 to +89 | | 12 | 8 | | 4 | | | | |
| | <1 | | | 0 | | 0 | | 0 | 0 |
| | 1-2.5 | | | 2 | | 1 | 3 | 3 | 6 |
| | >1 | | | 8 | | 0 | 8 | 4 | 0 |
| | >2.5 | | | 6 | | 3 | 9* | 1 | 2 |
| +90 to +150 | | 16 | 12 | | 4 | | | | |
| | <1 | | | 1 | | 2 | 3 | 2 | 11 |
| | 1-2.5 | | | 2 | | 2 | 4 | 2 | 10 |
| | >1 | | | 11 | | 2 | 13 | 2 | 1 |
| | >2.5 | | | 9 | | 4 | 13* | 0 | 3 |

*Optimum based on balanced maximum correct and minimum error

TABLE II $\frac{PW}{PH}$ RATIOS

| PREBREEDING | | POSTBREEDING | | | | | | | |
|---|---|---|---|---|---|---|---|---|---|
| | | +2 to +22 days | | +23 to +59 days | | +60 to +89 days | | +90 to +150 days | |
| −17 to +2 days | HEAT (−1 to +1 day) | Did Not Calve | Calved | Did Not Calve | Calved | Did Not Calve | Calved | Did Not Calve | Calved |
| .35 | .35 | .25 | .95 | .25 | .55 | 1.4 | 1.25 | .45 | .6 |
| .5 | .4 | .82 | 1.3 | .72 | 1.1 | 1.5 | 2.35 | .75 | 1.4 |
| .75 | .4 | .9 | 1.45 | .8 | 1.3 | 1.6 | 2.7 | 1.3 | 1.55 |
| 1.0 | .42 | 1.1 | 1.6 | .95 | 1.35 | 14.3 | 2.9 | 1.7 | 2.95 |
| 1.15 | .5 | 1.85 | 1.7 | 1.0 | 1.4 | | 4.5 | | 3.2 |
| 1.2 | .6 | 1.9 | 2.4 | 1.15 | 1.4 | | 7.5 | | 4.1 |
| 1.6 | .8 | 2.1 | 5.2 | 1.2 | 1.5 | | 11.4 | | 4.8 |
| 1.7 | .8 | 2.2 | | 1.35 | 1.95 | | 19.25 | | 5.3 |
| 1.75 | .9 | 3.7 | | 1.4 | 2.1 | | | | 7.5 |
| 2.15 | 1.0 | 4.1 | | 1.4 | 4.5 | | | | 12.5 |
| 2.4 | 1.1 | 5.2 | | 1.55 | 8.7 | | | | 16.15 |
| | | 6.15 | | 1.7 | | | | | 18.9 |
| | | 9.2 | | 1.7 | | | | | |
| | | | | 1.7 | | | | | |
| | | | | 2.1 | | | | | |
| | | | | 3.5 | | | | | |
| | | | | 7.1 | | | | | |
| | | | | 8.7 | | | | | |
| | | | | 9.3 | | | | | |
| | | | | 12.1 | | | | | |

In view of the above, it will be seen that the several objects of the invention are achieved and other advantageous results attained.

As various changes could be made in the above methods without departing from the scope of the invention, it is intended that all matter contained in the above description or shown in the accompanying drawings shall be interpreted as illustrative and not in a limiting sense.

What is claimed is:

1. The method for determining pregnancy or reproductive status in a mammal which comprises the steps of:
   a. obtaining at periodic time intervals mucus samples from the cervix of a mammal whose reproductive status is to be determined;
   b. obtaining nuclear magnetic resonance spectra of said samples;
   c. determining the nuclear magnetic resonance ratios from said spectra on the basis of the relationship $$\frac{\text{peak width at half amplitude}}{\text{peak height}}$$

and
   d. evaluating the reproductive status of said mammal from said ratios.

2. The method of claim 1 wherein the nuclear magnetic resonance spectra are obtained utilizing a nuclear magnetic resonance spectrometer operated at a frequency of between approximately 60 MHz and 200 MHz.

3. The method of claim 2 wherein the nuclear magnetic resonance spectrometer is operated at a frequency of approximately 60 MHz.

4. The method of claim 1 wherein the samples obtained from the cervix of said mammal approximate 0.1 ml.

5. The method of claim 1 wherein said mucus samples are at a temperature of from approximately 4° C. to 40° C. when the nuclear magnetic resonance spectra are obtained.

6. The method of claim 5 wherein the temperature of said samples is approximately 20° C. when the nuclear magnetic resonance spectra are obtained.

7. The method of claim 1 wherein the ratio of peak width at half amplitude to peak height of said spectra is at a higher value indicating pregnancy of said mammal.

8. The method of claim 1 wherein the ratio of peak width at half amplitude to peak height of said spectra is at a low value indicating the onset of estrus or impending termination of pregnancy in said mammal.

* * * * *